United States Patent [19]
Takeda et al.

[11] Patent Number: 5,540,081
[45] Date of Patent: Jul. 30, 1996

[54] PIPETTING APPARATUS WITH CLOT DETECTION

[75] Inventors: Masaaki Takeda; Hitomi Katagi; Yuko Kato; Junichi Kawanabe, all of Mitaka, Japan

[73] Assignees: Abbott Laboratories, Abbott Park, Ill.; Aloka Co., Ltd, Mitaka, Japan

[21] Appl. No.: 416,833

[22] PCT Filed: Aug. 31, 1993

[86] PCT No.: PCT/JP93/01227

§ 371 Date: May 15, 1995

§ 102(e) Date: May 15, 1995

[87] PCT Pub. No.: WO95/06878

PCT Pub. Date: Mar. 9, 1995

[51] Int. Cl.$^6$ .................................................. G01B 13/00
[52] U.S. Cl. .......................... 73/37; 340/626; 73/863.01
[58] Field of Search ................................. 73/37, 864.11, 73/863.01; 340/611, 626; 422/100

[56] References Cited

U.S. PATENT DOCUMENTS 4,430,886  2/1984  Rood ............................................ 73/37
4,675,301  6/1987  Chasneski et al. ..................... 73/863.01

FOREIGN PATENT DOCUMENTS

| 56-164957 | 12/1981 | Japan . |
| 6224151 | 2/1987 | Japan . |
| 6220372 | 2/1987 | Japan . |
| 1219564 | 9/1989 | Japan . |
| 2184762 | 7/1990 | Japan . |

*Primary Examiner*—Robert Raevis
*Attorney, Agent, or Firm*—Mark C. Bach

[57] ABSTRACT

A pipetting apparatus is provided with clot detection. The pipetting apparatus comprises a nozzle for aspirating a sample. A pressure sensor is connected with the nozzle for measuring pressure in said nozzle. A plurality of pressure difference calculating circuits are operatively connected with the pressure sensor, each for inputting an output of said pressure sensor and obtaining a pressure difference at a different pressure calculation period, respectively. A plurality of discriminating circuits each having a different discrimination threshold value determined according to each of the pressure calculation periods are provided. An alarm circuit is included for outputting a clot detection alarm signal when at least one of said discriminating circuits discriminates that the obtained pressure difference exceeds the discrimination threshold value.

1 Claim, 2 Drawing Sheets

PIPETTING APPARATUS WITH CLOT DETECTION

BACKGROUND OF THE INVENTION

Embodiments described herein relate to clot detection in a pipetting apparatus, and more particularly relate to the detection of clot caused when substance in a liquid sample is adhered to a tip portion of a sampling nozzle, for instance.

In testing of a sample, it is desirable to perform pipetting operation which obtains any required volume of the sample by aspiration. In general, the pipetting operation is carried out by inserting a nozzle connected to a suction pump into the sample contained in a test tube or the like to aspirate and obtain a required volume of the sample. As an apparatus for performing the pipetting operation, a pipetting apparatus is well known.

Recently, in particular, an automatic pipetting apparatus has been widely used, in which the respective pipetting processes can be carried out automatically and continuously without assistance of an operator.

In the automatic pipetting apparatus as described above, the constituents of blood such as serum or plasma collected from a living body is often used as a sample to be pipetted. The pipetted sample is mixed with a chemical reagent or others to carry out a predetermined test.

The blood serum or plasma is obtained from blood by a centrifugal separation, and in many cases thus obtained serum or plasma is used as it is for the sample. When thus obtained blood sample is pipetted, there is a problem in that the tip portion of the nozzle is likely to be clotted with foreign matters such as solid substance or fibrous substance contained in the sample or a serum separating medium, thus resulting in a clotting condition. When the pipetting operation is carried out under the clotting condition, there arises a problem in that the accuracy of pipetting is deteriorated.

In view of this problem, a method for detecting clot caused in an automatic pipetting apparatus has been proposed in Japanese Laid-open Patent Publication No. 2184762. In this conventional method, the pressure within the nozzle is detected by a pressure sensor. Changes in pressure detected by the pressure sensor are monitored. The clotting condition can be detected when waveform indicating the pressure changes shifts to a negative value side abruptly. In more detail, the pressure is sampled for each predetermined period, and the difference between the current detected pressure and the preceding detected pressure is compared with a threshold value to discriminate the clotting condition.

In the conventional pipetting apparatus, however, the sampling period is set short in order to detect the clotting condition as soon as possible, and further since the threshold value is determined so as to correspond to the short sampling period. For this reason, there is a problem in that it is difficult to detect an imperfect clotting condition, because under the imperfect clotting condition the pressure change is so small as not to be detectable by this detecting method of the conventional pipetting apparatus. Therefore, in the conventional apparatus, there is a problem that, when the pipetting accuracy is deteriorated due to such imperfect clotting condition, it has been difficult to detect such undesirable condition.

In order to overcome the above-mentioned problems, it is desirable to provide an automatic pipetting apparatus which can detect imperfect clotting conditions as well as perfect clotting condition.

SUMMARY OF THE INVENTION

A pipetting apparatus is provided with clot detection. The pipetting apparatus comprises a nozzle for aspirating a sample. A pressure sensor is connected with the nozzle for measuring pressure in said nozzle. A plurality of pressure difference calculating circuits are operatively connected with the pressure sensor, each for inputting an output of said pressure sensor and obtaining a pressure difference at a different pressure calculation period, respectively. A plurality of discriminating circuits each having a different discrimination threshold value determined according to each of the pressure calculation periods are provided. An alarm circuit is included for outputting a clot detection alarm signal when at least one of said discriminating circuits discriminates that the obtained pressure difference exceeds the discrimination threshold value.

DETAILED DESCRIPTION OF PREFERRED EMBODIMENTS

Embodiments of the present invention are generally characterized by a pipetting apparatus provided with clot detection, which comprises: a nozzle for aspirating a sample; a pressure sensor for measuring pressure in the nozzle; a plurality of pressure difference calculating circuits each for inputting an output of the pressure sensor and obtaining a pressure difference at a different pressure calculation period, respectively; a plurality of discriminating circuits each having a different discrimination threshold value determined according to each of the pressure calculation periods; and an alarm circuit for outputting a clot detection alarm signal when at least one of the discriminating circuits discriminates that the obtained pressure difference exceeds the discrimination threshold value.

In the construction as described above, the pressure in the nozzle can be detected directly or indirectly by the pressure sensor, and the measured pressure value is transmitted to a plurality of pressure difference calculating circuits. Each of the pressure difference calculating circuits has its own different pressure calculation period, so that the pressure difference can be obtained for each calculation period. A plurality of the pressure differences thus obtained are transmitted to the corresponding discriminating circuits for comparison with the predetermined threshold values, respectively. Further, when at least one of the discriminating circuits discriminates the presence of clotting condition, the alarm circuit outputs a clot detection alarm signal. In the pipetting apparatus described herein, since there are provided a plurality of calculation periods which monitor the pressure respectively, pressure waveforms indicative of imperfect clotting conditions in addition to the pressure waveform indicative of the perfect clotting condition can be discriminated, thus enabling a further fine clot detection.

Figure 1:
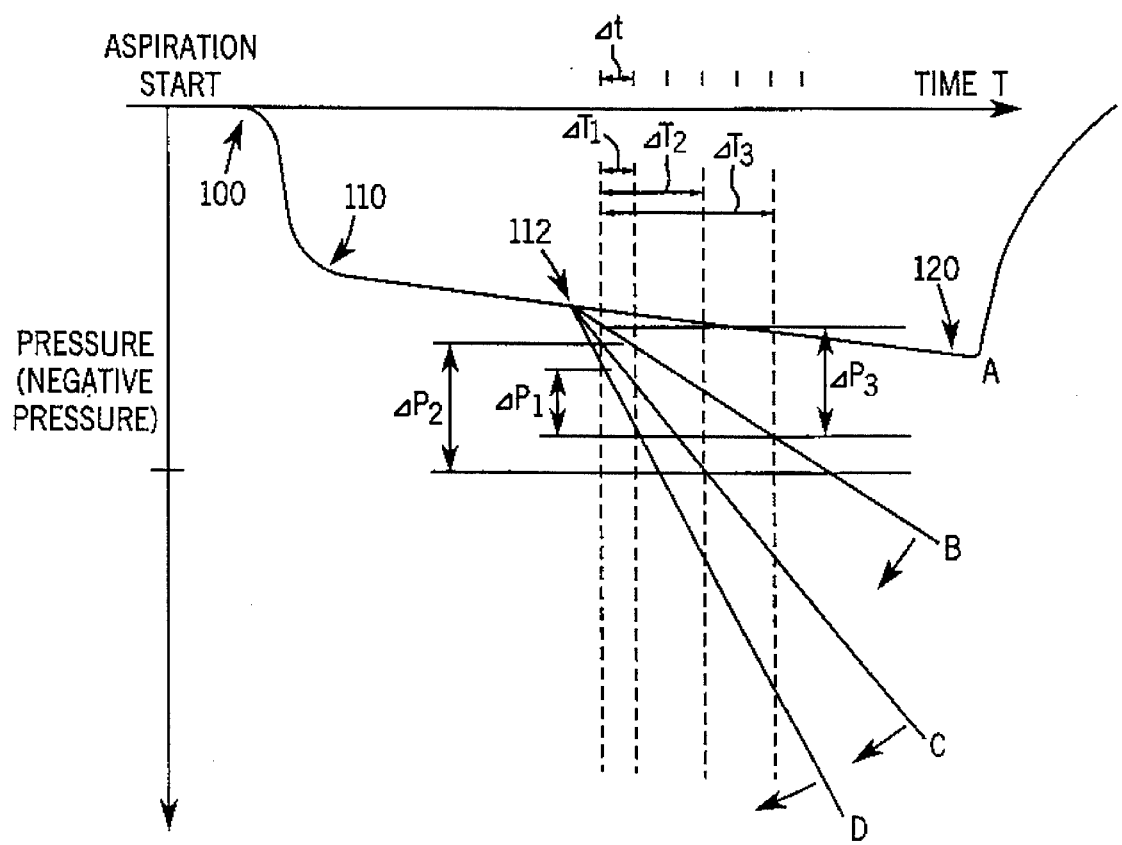
FIG. 1 is an aspiration waveform diagram for assistance in explaining the principle of clot detection according to the present invention.

Referring initially to FIG. 1, pressure waveforms obtained when a sample is aspirated by a nozzle are represented, in which the abscissa indicates the time and the ordinate indicates the pressure (e.g. negative pressure). When the aspiration begins at the time indicated by the numeral 100 in FIG. 1, the pressure in the nozzle changes into the negative pressure side sharply. Thereafter, when no clotting condition occurs, the pressure changes gradually for a constant time period between the time point 110 and the time point 120 as shown by the line A. On the other hand, when the nozzle is clotted perfectly, the pressure waveform descends abruptly and the pressure changes into the negative pressure side greatly as shown by the line D, immediately after the clotting condition occurs. In the conventional apparatus, only the sharp inclination as shown by the line D has been detected.

In practice, however, the nozzle clotting condition is caused by various ways. Namely, there are cases that the nozzle is clotted momentarily and perfectly and that the nozzle is clotted gradually. Further, there is a case that the sample flows at an extremely slow speed although the nozzle is not clotted. Therefore, it is impossible to maintain a high pipetting accuracy only by monitoring the pressure waveform as shown by the line D.

One embodiment of the apparatus disclosed herein uses a plurality of the pressure difference calculation periods to obtain the pressure difference at each of the calculation periods. The obtained pressure differences are compared with the threshold values determined according to the respective calculation periods, respectively, so that both the perfect and imperfect clotting conditions can be detected.

The lines B and C shown in FIG. 1 represent the pressure waveforms caused by the imperfect clotting conditions. In order to detect such waveforms as described above, it is necessary to set the calculation period to a relatively long time. This is because the waveforms beginning from a clot generation point 112 fluctuate up and down irregularly, although they are indicated by straight lines in FIG. 1. Therefore, it becomes possible to detect the clotting conditions reliably only when the calculation time period is set to a relatively long time.

Accordingly, in the disclosed pipetting apparatus, when the perfect clotting condition as shown by the line D is required to be detected, the pressure difference $\Delta P_1$ between the preceding pressure and the current pressure is obtained for each predetermined sampling time $\Delta t$ ($=\Delta T_1$) in the same way as with the case of the conventional apparatus. Further, in order to detect imperfect clotting conditions, the pressure change rate is obtained on the basis of the gradient of the lines B or C for the calculation periods which are integer times longer than the sampling time $\Delta t$. As a result, the imperfect clotting condition can be detected based on the obtained pressure difference which is larger than $\Delta P_1$.

In more detail, in FIG. 1, in the case of the imperfect clotting condition as shown by C, the pressure difference $\Delta P_2$ is obtained for the calculation period $\Delta T_2$ (e.g., 3×$\Delta t$); and in the case of the imperfect clotting condition as shown by B, the pressure difference $\Delta P_3$ is obtained for the calculation period $\Delta T_3$ (e.g., 5×$\Delta t$).

Figure 2:
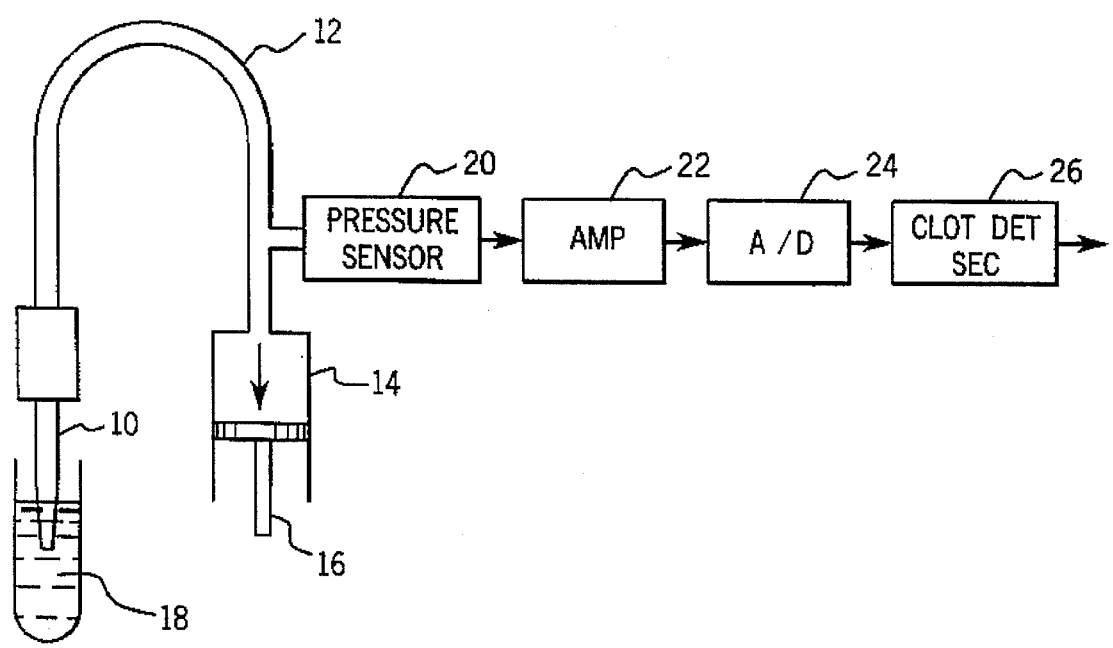
FIG. 2 is a block diagram showing the entire configuration of the pipetting apparatus according to the present invention.

FIG. 2 is a block diagram showing another embodiment of the pipetting apparatus. In the drawing, a nozzle 10 for aspirating a sample is connected to a pump 14 through an air hose 12. When a piston 16 is extracted from the pump 14, the inner pressure within the air hose 12 and the nozzle 10 is reduced, so that the sample 18 can be aspirated. At this point, the pressure is detected by a pressure sensor 20 connected to the air hose 12. The detected pressure signal is amplified by an amplifier 22, and converted into a digital signal by an A/D converter 24. The converted digital signal is then supplied to a clot detecting section 26.

Figure 3:
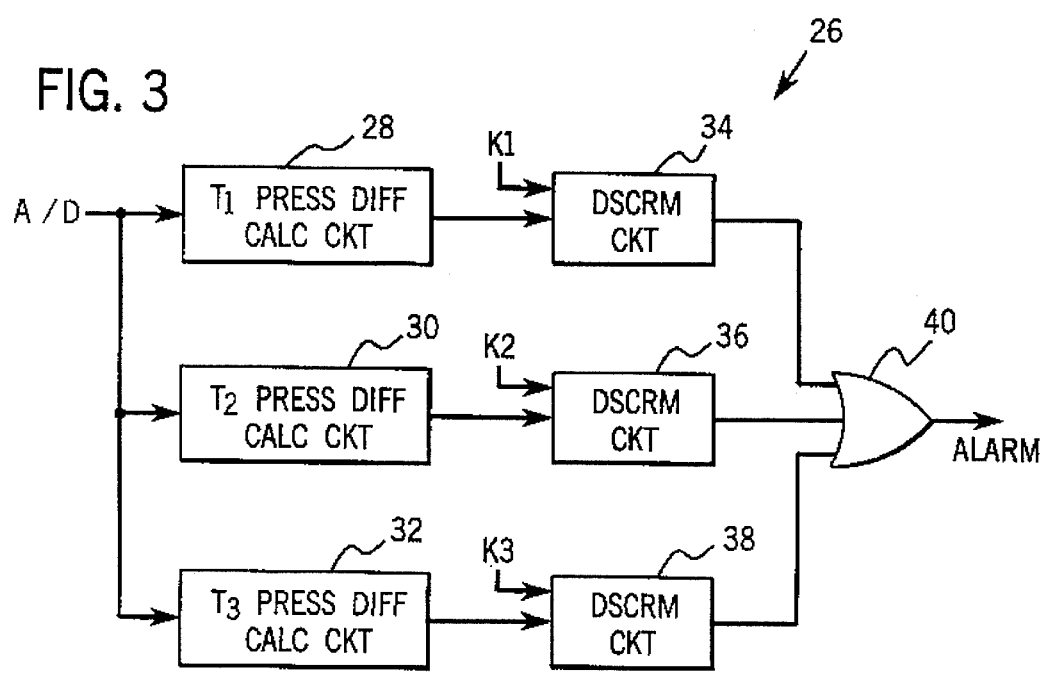
FIG. 3 is a block diagram showing the practical circuit configuration in the clot detection section 26.

FIG. 3 is a block diagram showing the practical configuration of the clot detecting section 26, in which three calculation periods are provided by way of example.

In this embodiment, the output signal of the A/D converter 24 is inputted to three pressure difference calculating circuits 28, 30 and 32. The calculating circuit 28 calculates the pressure difference for each sampling time $\Delta t$ ($=\Delta T_1$); the calculating circuit 30 calculates the pressure difference in the calculation period $\Delta T_2$; and the calculating circuit 32 calculates the pressure difference in the calculation period $\Delta T_3$, respectively. In each of the calculating circuits 28, 30 and 32, the pressure difference is also calculated for each sampling time $\Delta t$, and the calculated results are updated, respectively. The output of each of the calculating circuits 28, 30 and 32 is transmitted to each of three pressure change rate discriminating circuits 34, 36 and 38 connected to the corresponding calculating circuits 28, 30 and 32, respectively. In the pressure change rate discriminating circuits, each of the transmitted outputs is compared with each of predetermined threshold values K1, K2 and K3 which have been set so as to correspond to the respective calculation periods, respectively. In this case, since the calculation period $\Delta T_1$ is extremely short, a relatively large threshold value K1 is set to detect a sharp inclination of a waveform. On the other hand, the threshold value K3 corresponding to the calculation period $\Delta T_3$ is set into a relatively small value so as to be able to detect imperfect clotting condition caused when the nozzle is being gradually clotted, for instance. Further, the threshold value K2 is set into the substantially midvalue between the threshold values K1 and K3.

In case any of the pressure change rate discriminating circuits discriminates "perfect clot" or "imperfect clot", an OR gate 40 generates an alarm signal, so that an alarm circuit (not shown) provided at the rear stage of the discriminating circuits is activated to generate a buzzer sound or display a predetermined alarm display. Further, it is also possible to separate the adhered substance from the nozzle by stopping the aspirating operation and further dispensing a small volume of the aspirated liquid sample from the nozzle.

Further, in the above-mentioned embodiments, three calculation periods are determined. Without being limited thereto, however, it is of course possible to provide four or more calculation periods. When the number of the calculation periods increases, it becomes possible to detect the clotting condition in more fine way, thus enabling to further improve the pipetting accuracy.

Since a plurality of calculation periods are set, it is possible to detect not only the perfect clotting condition but also imperfect clotting condition, thus enabling a fine clot detection and thereby improving pipetting accuracy.

What is claimed is:

1. A pipetting apparatus provided with clot detection, the pipetting apparatus comprising:
   (a) a nozzle for aspirating a sample;
   (b) a pressure sensor connected with the nozzle for measuring pressure in said nozzle;
   (c) a plurality of pressure difference calculating circuits operatively connected with the pressure sensor, each for inputting an output of said pressure sensor and obtaining a pressure difference at a different pressure calculation period, respectively;
   (d) a plurality of discriminating circuits each having a different discrimination threshold value determined according to each of the pressure calculation periods; and
   (e) an alarm circuit for outputting a clot detection alarm signal when at least one of said discriminating circuits discriminates that the obtained pressure difference exceeds the discrimination threshold value.

* * * * *